(12) United States Patent
Poindexter et al.

(10) Patent No.: US 6,348,472 B1
(45) Date of Patent: Feb. 19, 2002

(54) NPY ANTAGONISTS: SPIROISOQUINOLINONE DERIVATIVES

(75) Inventors: Graham S. Poindexter, Old Saybrook; Ildiko Antal, Cheshire; Leah M. Giupponi, Glastonbury; Robert H. Stoffel, Hamden; Marc A. Bruce, Wallingford, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/586,146

(22) Filed: Jun. 2, 2000

Related U.S. Application Data
(60) Provisional application No. 60/150,774, filed on Aug. 26, 1999.

(51) Int. Cl.⁷ .................... C07D 471/10; A61K 31/438
(52) U.S. Cl. .......................................... 514/278; 546/18
(58) Field of Search ............................. 546/18; 514/278

(56) References Cited

U.S. PATENT DOCUMENTS

| | | | |
|---|---|---|---|
| 3,301,857 A | 1/1967 | Berger et al. ................. | 546/18 |
| 5,554,621 A | 9/1996 | Poindexter et al. ......... | 514/278 |
| 6,054,590 A | 4/2000 | Poindexter et al. ...... | 548/311.1 |
| 6,063,934 A | 5/2000 | Poindexter et al. ...... | 548/323.5 |
| 6,096,745 A | 8/2000 | Poindexter et al. .... | 514/252.05 |

OTHER PUBLICATIONS

Gehlert and Hipskind, *Exp. Opin. Invest. Drugs*, 1997, 6, pp. 1827–1838.

*Primary Examiner*—Alan L. Rotman
(74) *Attorney, Agent, or Firm*—Richard R. Ryan

(57) ABSTRACT

A series of non-peptidergic antagonists of NPY have been synthesized and are comprised of spiroisoquinolinone derivatives of Formula I.

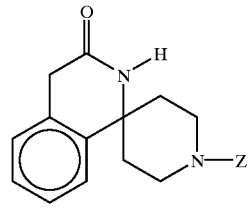

I

As antagonists of NPY-induced feeding behavior, these compounds and known analogs are expected to act as effective anorexiant agents in promoting weight loss and treating eating disorders.

10 Claims, No Drawings

NPY ANTAGONISTS: SPIROISOQUINOLINONE DERIVATIVES

CROSS REFERENCE TO RELATED APPLICATION

This non-provisional application claims priority from provisional application U.S. serial no. 60/150,774 filed Aug. 26, 1999.

BACKGROUND OF THE INVENTION

The present invention concerns heterocyclic carbon compounds comprising spiroisoquinolinone derivatives which have been discovered to be NPY antagonists.

Antagonism of neuropeptide Y receptors has been postulated to reduce food consumption in mammals. Several non-peptidic chemotypes have been disclosed in the literature as being antagonists at the $Y_1$ and at the $Y_5$ subtypes of NPY receptors. (See Gehlert and Hipskind, *Exp. Opin. Invest. Drugs*, 1997, 6, pp. 1827–1838.)

Neither applicants' novel spiroisoquinolinone compounds nor the use of these and related spiroisoquinolinones for use in treating medical disorders by means of antagonizing NPY receptors following administration of these compounds is known or suggested by prior art.

Earlier work by our group involved 4-(3-substituted-phenyl)-1,4-dihydropyridine derivatives having NPY antagonist properties. These derivatives conform to structural formula (1).

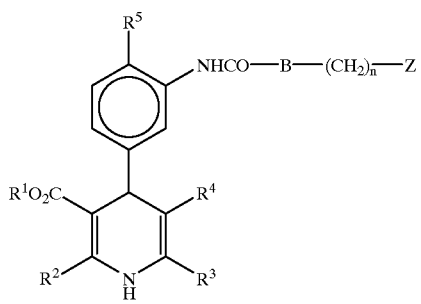

(1)

In (1) B is either a covalent bond or the group —NH—. The symbol Z denotes hetaryl moieties, examples being piperidine or piperazine.

In U.S. Pat. No. 5,554,621, Z is a fused ring or spiro-fused nitrogen heterocyclic group giving rise to compounds having, for example, a structure such as formula (2).

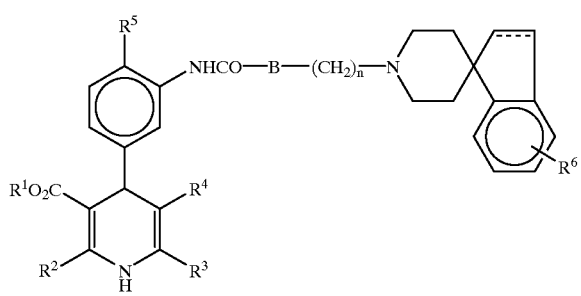

(2)

Other work by our group has resulted in discovery of certain imidazolone derivatives of formula (3) having NPY antagonism (cf: U.S. Ser. No. 60/079,359).

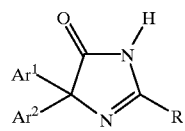

(3)

As can be seen, these compounds differ significantly in structure from the compounds of the present invention.

SUMMARY AND DETAILED DESCRIPTION OF THE INVENTION

The present invention comprises compounds of Formula I, their

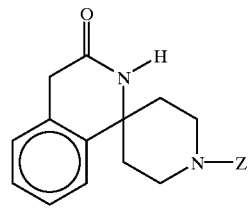

I pharmaceutically acceptable acid addition salts and/or their hydrates thereof. In the foregoing structural Formula I, the symbol Z has the following meanings.

Z can be a $C_{9-10}$alkyl, a $C_{2-6}$alkenyl group or the moiety A—R, in which A denotes a $C_{1-6}$ linking alkanediyl or $C_{2-6}$alkenediyl group connecting R to the piperidino-ring nitrogen atom.

R, in turn, is selected from —OH, —CH(OMe)$_2$, —NR$^1$R$^2$, 1-adamantyl,

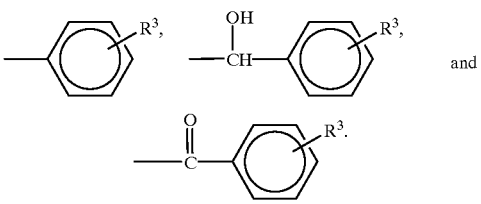

and $R^1$ and $R^2$ are independently chosen from hydrogen, $C_{1-4}$alkyl, or benzyl groups, $R^3$ is selected from hydrogen, $C_{1-4}$alkyl, $C_{1-4}$alkoxy, halogen, —NR$^1$, R$^2$, phenyl, phenoxy, and —O$_2$C-phenyl.

In preferred compounds, A is a methylene or ethylene chain and R

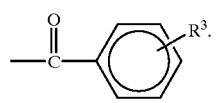

In more preferred compounds, R is

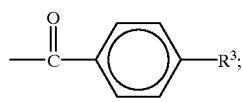

and in most preferred compounds, $R^3$ is phenyl or phenoxy.

The present invention also pertains to pharmaceutically acceptable salts of the Formula I compounds. Such salts include those derived from organic and inorganic acids such as, without limitation, hydrochloric, hydrobromic, phosphoric, sulfuric, methanesulfonic, acetic, fumaric, tarytaric, moleic, succinic, lactic, citric acid, and the like.

Formula I compounds can be produced by using the general process shown in Scheme 1. The symbol Z is as previously defined.

Scheme 1
General Synthesis of Spirosoquinolinone Derivatives

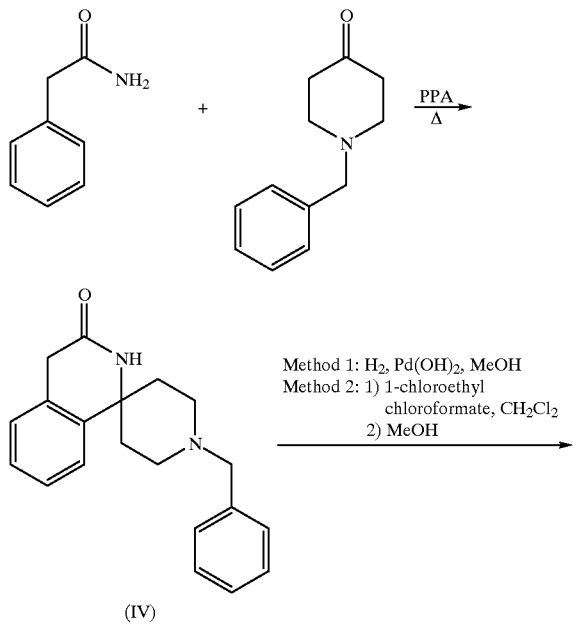

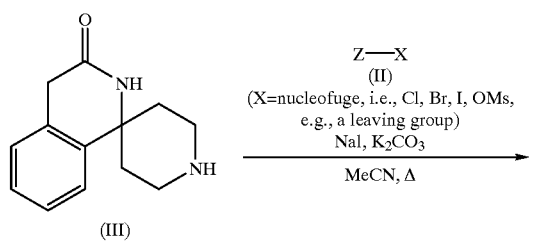

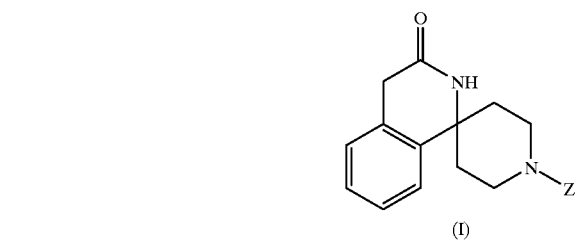

The majority of Formula I compounds were synthesized by the route shown in Scheme 1.

For Formula I products wherein Z is

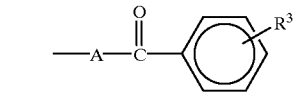

and A is at least three carbons in length, the synthetic process involves protection of the carbonyl moiety and in most instances straightforward ketal formation accomplishes this objective, as shown in Scheme 2.

Scheme 2
Synthesis of Alkyl Phenyl Ketone Derivatives

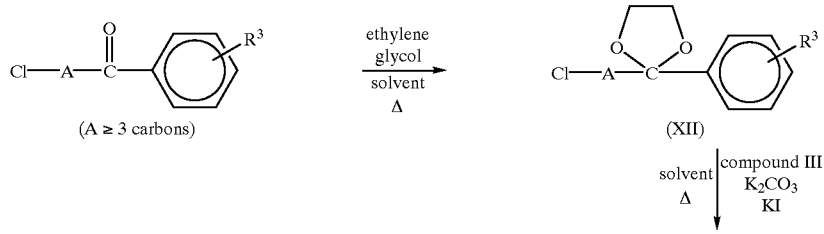

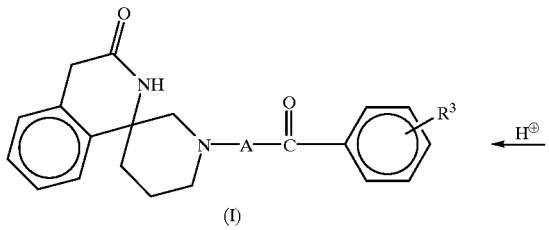

(I)

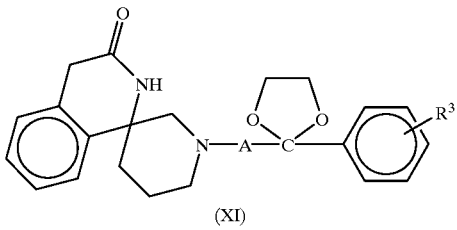

(XI)

Since structural diversity arises from the variation of Z, Formula II alkylating agents are the focus for synthetic elaboration. Many of the Formula II compounds are either commercially available or amenable to synthetic methods. Scheme 3 illustrates synthesis of Z—X compounds wherein Z is R—A- and R is, e.g.

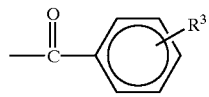

with $R^3$ being phenoxy.

Scheme 3
Synthesis of Diphenyl Ether Type Alkylating Agents

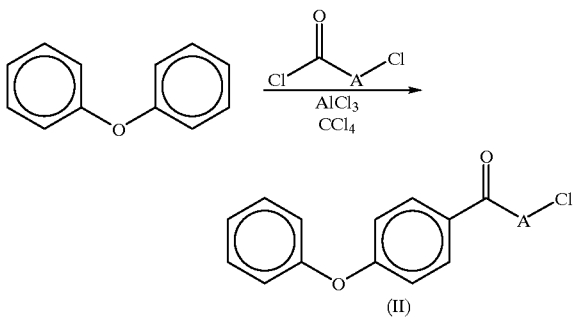

(II)

Another synthetic variation of the Formula I structure can be obtained by operation on a Formula I compound itself. This is illustrated in Scheme 4 where a Suzuki coupling is employed.

Scheme 4
Synthesis Elaboration of Formula I Products

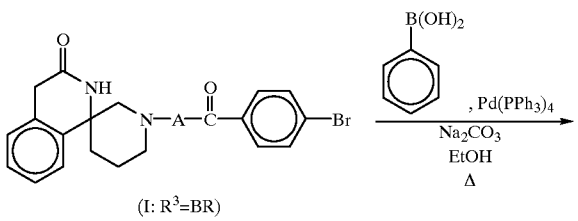

(I: $R^3$=BR)

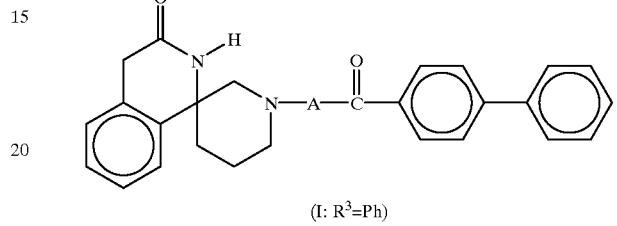

(I: $R^3$=Ph)

Similar processes employing synthetic modifications familiar to one skilled in the art of synthetic organic chemistry can be utilized to provide additional Formula I compounds. Additional examples and procedures are provided infra in the Specific Embodiments section of the specification.

The compounds of Formula I demonstrate binding affinity at NPY receptors. The binding interaction has been characterized as antagonism at NPY $Y_5$ receptors. This pharmacologic activity was characterized by using BRI-TN-5BI-4 insect cells infected with NPY $Y_5$-recombinant Baculovirus. These cells which express $Y_5$ receptor were used in a radioligand binding assay employing Iodine-125 labeled PYY ligand. The spiroisoquinolones of this invention all showed $IC_{50}$ values of less than 10 μM, with preferred compounds having $IC_{50}$ values of less than 500 nM and most preferred compounds having $IC_{50}$ values of less than 100 nM.

Certain preferred compounds of Formula I were tested in a functional assay where they were found to antagonize NPY-mediated inhibition of forskolin-induced c-AMP accumulation in HEK-293 cells.

Pharmacologically, these compounds act as selective NPY antagonists at NPY $Y_5$ receptor sites. As such, the compounds of Formula I are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulemia, and metabolic disorders;

diseases related to sexual dysfunction and reproductive disorders;

conditions or disorders associated with inflammation;

respiratory diseases, such as asthma and conditions related to asthma and bronchoconstriction;

diseases related to abnormal hormone release, such as leutinizing hormone, growth hormone, insulin and prolactin;

sleep disturbance and diabetes;

emesis.

There is evidence that NPY contributes to certain symptoms in these disorders: hypertension, eating disorders, and depression/anxiety; as well as circadian rhythms. Compounds of this invention are expected to be useful in treating these disorders as well as sleep disturbance and diabetes.

Selected compounds are tested further for their ability to block or stimulate NPY-induced feeding in test animals by intraperitoneal administration to the animal prior to inducing feeding behavior with NPY. Taken together, these tests indicate that the compounds of this invention would be useful anorexiants and would function as anti-obesity agents with further use in various clinical eating disorders. Thus, another aspect of the invention concerns a process for reducing food intake in an obese mammal or a mammal with an eating disorder. The process comprises systemic administration to such a mammal of an anorexiant-effective dose of a compound of Formula I or a pharmaceutically acceptable acid addition salt and/or hydrate thereof.

On the basis of pharmacologic testing, an effective dose given parenterally could be expected to be in a range of about 0.05 to 1 mg/kg body weight and if given orally would be expected to be in the range of about 1 to 20 mg/kg body weight.

For clinical applications, however, the dosage and dosage regimen must in each case be carefully adjusted, utilizing sound professional judgment and considering the age, weight and condition of the recipient, the route of administration and the nature and gravity of the illness. Generally, the compounds of the instant invention will be administered in the same manner as for available anorexiant drugs such as Diethylpropion, Mazindol, or Phentermine and the daily oral dose would comprise from about 70 to about 1400 mg, preferably 500 to 1000 mg administered from 1 to 3 times a day. In some instances, a sufficient therapeutic effect can be obtained at lower doses while in others, larger doses will be required.

The term systemic administration as used herein refers to oral, buccal, transdermal, rectal, and parenteral (i.e. intramuscular, intravenous, and subcutaneous) routes. Generally, it will be found that when a compound of the present invention is administered orally, which is the preferred route, a larger quantity of reactive agent is required to produce the same effect as a smaller quantity given parenterally. In accordance with good clinical practice, it is preferred to administer the instant compounds at a concentration level that will produce effective anorectic effects without causing any harmful or untoward side effects. Similarly, the instant compounds can be administered to treat the various diseases, conditions, and disorders listed supra.

Therapeutically, the instant compounds are generally given as pharmaceutical compositions comprised of an effective anorectic amount of a compound of Formula I or a pharmaceutically acceptable acid addition salt thereof and a pharmaceutically acceptable carrier. Pharmaceutical compositions for effecting such treatment will contain a major or minor amount, e.g. from 95 to 0.5% of at least one compound of the present invention in combination with the pharmaceutical carrier, the carrier comprising one or more solid, semi-solid, or liquid diluent, filler, and formulation adjuvant which is non-toxic, inert and pharmaceutically acceptable. Such pharmaceutical compositions are preferably in dosage unit forms; i.e., physically discrete units containing a predetermined amount of the drug corresponding to a fraction or multiple of the dose which is calculated to produce the desired therapeutic response. The dosage units can contain 1, 2, 3, 4, or more single doses, or, alternatively, one-half, one-third, or one-fourth of a single dose. A single dose preferably contains an amount sufficient to produce the desired therapeutic effect upon administration at one application of one or more dosage units according to the pre-determined dosage regimen usually a whole, half, third, or quarter of the daily dosage administered once, twice, three, or four times a day. Other therapeutic agents can also be present. Pharmaceutical compositions which provide from about 50 to 1000 mg of the active ingredient per unit dose are preferred and are conventionally prepared as tablets, lozenges, capsules, powders, transdermal patches, aqueous or oily suspensions, syrups, elixirs, and aqueous solutions. Preferred oral compositions are in the form of tablets or capsules and may contain conventional excipients such as binding agents (e.g. syrup, acacia, gelatin, sorbitol, tragecanth, or polyvinylpyrrolidone), fillers (e.g. lactose, sugar, maize-starch, calcium phosphate, sorbitol, or glycine), lubricants (e.g. magnesium stearate, talc, polyethylene glycol or silica), disintegrants (e.g. starch) and wetting agents (e.g. sodium lauryl sulfate). Solutions or suspensions of a Formula I compound with conventional pharmaceutical vehicles are generally employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyetheleneglycols or mixtures thereof. The polyethyleneglycols consist of a mixture of non-volatile, usually liquid, polyethyleneglycols which are soluble in both water and organic liquids and which have molecular weights from about 200 to 1500.

DESCRIPTION OF THE SPECIFIC EMBODIMENTS

The compounds which constitute this invention and their methods of preparation will appear more fully from a consideration of the following examples which are given for the purpose of illustration only and are not to be construed as limiting the invention in sphere or scope.

General Comments

All catalytic hydrogenations were performed with Parr Hydrogenators (Parr Instrument Co.). Bulb-to-bulb distillations were carried out on a Kugelrohr apparatus (Aldrich). Solvate removal from solids, when noted, as accomplished by drying under vacuum overnight in an Abderhalden drying pistol over refluxing EtOH at 78° C. All melting points were obtained using a Thomas-Hoover melting point apparatus and are uncorrected. $^1$H and $^{13}$C NMR were obtained using a Bruker AM-300 NMR spectrometer at 300 and 75.5 MHz, respectively. NMR solvents used were deuterochloroform (CDCl$_3$), methyl-d$_6$-sulfoxide (DMSO-d$_6$), and deuterium oxide (D$_2$O). All mass spectra were obtained by Electrospray Ionization, unless stated otherwise. HPLC purity was determined on a Shimadzu HPLC.

HPLC Method for Determination of Purity

Start % B=0
Final % B=100
Gradient Time=4 min
Flow Rate=4 mL/min
Wavelength=220
Solvent A=10% MeOH-90% H$_2$O-0.1% TFA
Solvent B=90% MeOH-10% H$_2$O-0.1% TFA
Column=YMC C18 S5 4.6×50 mm I. Synthesis of Intermediates
A. Compound III—Piperidino Spiroisoquinolone

EXAMPLE 1

Synthesis of Benzylpiperidine-Spiroisoquinolone (IV).

A 3-neck flask equipped with mechanical stirring containing a mixture of phenylacetamide (100 g, 740 mmol) and 1-benzyl-4-piperidone (140 g, 740 mmol) in polyphosphoric acid (1.5 kg) was heated at 100° C. under N$_2$ for 24 h. Ice (2 L) was then gradually added to dilute and cool the mixture. The cooled solution was neutralized to pH 7 by the gradual addition of NaOH pellets, adding ice as necessary to cool the solution. The neutralized solution was then extracted with CH$_2$Cl$_2$, and the solvent was removed in vacuo. The residue was recrystallized from i-PrOH (0.5 L) to give the crude product. This was taken up in CH$_2$Cl$_2$ (2.0 L) and MeOH (0.5 L) and refluxed until no more material would dissolve. This suspension was filtered hot, removing only polar impurities in the filtrate, and the filter cake was rinsed with hot water until all color had been removed. The filter cake was triturated in hot i-PrOH and then cooled, and the resulting solid was collected by filtration and dried overnight in a drying pistol to afford IV as a cream-colored solid (107 g, 47% yield). (Cf: Berger, et al., U.S. Pat. No. 3,301,857, 1967.)

EXAMPLE 2

Synthesis of Piperidine-Spiroisoquinolone (III). Method A

A solution of intermediate IV (9.5 g, 31 mmol) in MeOH (200 mL) containing 20% Pd(OH)$_2$ (Pearlman's catalyst, 5.0 g) was hydrogenated in a Parr apparatus at 60 psi for 64 h. Catalyst was removed by filtration over Celite, and the solvent was removed in vacuo from the filtrate. The residue was triturated in EtOAc, and the resulting white solid was collected by filtration to afford compound III (6.2 g, 93% yield). (Cf: U.S. Pat. No. 3,301,857, ibid).

EXAMPLE 3

Synthesis of Piperidine-Spiroisoquinolone (III). Method B

A solution of intermediate compound IV (1.0 eq) and Protol Sponge (Aldrich, 1.0 eq) in CH$_2$Cl$_2$ under N$_2$ was cooled to 10° C. A solution of 1-chloroethyl chloroformate (1.5 eq) in CH$_2$Cl$_2$ was added in a dropwise fashion over 30 min, and the reaction was stirred for 2 h while warming to room temperature. The reaction mixture was then subjected to chromatography by vacuum filtration (SiO$_2$:CH$_2$Cl$_2$/Acetone). The resulting white solid was then suspended in MeOH and refluxed for 30 min. The solvent was then removed in vacuo to afford the desired product as the hydrochloride salt (70% yield).

B. Formula II-Type Compounds
1. 2-Haloalkyl-2-Phenyl-1,3-dioxolanes (XII)

EXAMPLE 4

General Procedure for the Synthesis of Ketals (XII)

The selected 4-chlorobutyrophenones (5.0 mmol) were taken up in 50 mL toluene containing ethylene glycol (3.0 mL, 50 mmol) and p-toluenesulfonic acid monohydrate (4 mg), and were refluxed overnight, the water generated being collected in a Dean-Stark trap. The reaction mixtures were then cooled, then rinsed with water, and the organic extracts were dried (Na$_2$SO$_4$) and the solvent was removed in vacuo. The residues were then subjected to chromatography (SiO$_2$:CH$_2$Cl$_2$/)Hexanes) to isolate the desired ketals.

EXAMPLE 5

2-(3-Chloropropyl)-2-phenyl-1,3-dioxolane[1]

This compound was prepared using the procedure of Example 4 with 4-chlorobutyrophenone to give the expected product which was isolated as a colorless oil (68% yield): MS (DCl) m/z227 (MH$^+$); $^1$H NMR (CDCl$_3$) δ 7.43 (m, 2 H), 7.30 (m, 3 H), 4.01 (m, 2 H), 3.77 (m, 2 H), 3.52 (t, 2 H, J=6.6 Hz), 2.03 (m, 2 H), 1.85 (m, 2 H); $^{13}$C NMR (CDCl$_3$) δ 142.3, 128.3, 128.0, 125.7, 110.0, 64.6, 45.2, 37.8, 27.1. Anal. Calcd for C$_{12}$H$_{15}$ClO$_2$: C, 63.58; H, 6.67. Found: C, 63.44; H, 6.62.

[1]Wills, et al., *J. Org. Chem.*, 1980, 45, 2489–2498.

Using the above procedure with the appropriate 4-chlorobutyrophenone, the following (XII) compounds were prepared.

EXAMPLE 6

2-(3-Chloropropyl)-2-(4-methoxyphenyl)-1,3-dioxolane[2]

This compound was obtained as a white solid (41% yield): MS (DCl) m/z 257 (MH$^+$); $^1$H NMR (CDCl$_3$) δ 7.34 (d, 2 H, J=8.7 Hz), 6.85 (d, 2 H, J=9.0 Hz), 3.99 (m, 2 H), 3.79 (s, 3 H), 3.76 (m, 2 H), 3.51 (t, 2 H, J=6.6 Hz), 2.01 (m, 2 H), 1.82 (m, 2 H); $^{13}$C NMR (CDCl$_3$) δ 159.4, 134.5, 127.0, 113.6, 110.0, 64.6, 55.4, 45.3, 37.9, 27.2. Anal. Calcd for C$_{13}$H$_{17}$ClO$_3$: C, 60.82; H, 6.67. Found: C, 60.71; H, 6.55.

[2]Li, et al., *Huaxue Xuebao*, 1990, 48, 913–919.

EXAMPLE 7

2-(3-Chloropropyl)-2-(4-phenoxyphenyl)-1,3-dioxolane

This compound was furnished as a pale yellow oil (78% yield): MS (DCl) m/z 319.2 (MH$^+$); $^1$H NMR (CDCl$_3$) δ 7.36 (m, 4 H), 7.11 (t, 1 H, J=8.4 Hz), 7.02 (d, 2 H, J=7.8Hz), 6.96 (d, 2 H, J=8.7Hz), 4.01 (m, 2 H), 3.79 (m, 2 H), 3.54 (t, 2 H, J=6.9 Hz), 2.03 (m, 2 H), 1.85 (m, 2 H); $^{13}$C NMR (CDCl$_3$) δ 157.3, 157.0, 137.1, 129.9, 127.3, 123.6, 119.2, 118.3, 110.0, 64.7, 45.3, 37.9, 27.2.

EXAMPLE 8

2-(3-Chloropropyl)-2-(4-bromophenyl)-1,3-dioxolane[3]

This compound was isolated as a colorless oil (93% yield): MS (DCl) m/z 305, 307 (MH$^+$); $^1$H NMR (CDCl$_3$) δ 7.46 (d, 2 H, J=8.7 Hz), 7.32 (d, 2 H, J=8.7 Hz), 4.01 (m, 2 H), 3.74 (m, 2 H), 3.52 (t, 2 H, J=6.6 Hz), 1.98 (m, 2 H), 1.81 (m, 2 H); $^{13}$C NMR (CDCl$_3$) δ 141.6, 131.5, 127.6, 122.2, 109.7, 64.7, 45.1, 37.7, 27.0. Anal. Calcd for C$_{12}$H$_{14}$BrClO$_2$: C, 47.16; H, 4.62. Found: C, 47.45; H, 4.63.

[3]Knoz, et al., European Patent Application EP47923A, 1981.

EXAMPLE 9

2-(3-Chloropropyl)-2-(4-chlorophenyl)-1,3-dioxolane[4]

This compound was obtained as a colorless oil (40% yield): MS (DCl) m/z 261, 263 (MH$^+$); $^1$H NMR (CDCl$_3$) δ 7.37 (d, 2 H, J=8.4 Hz), 7.29 (d, 2 H, J=8.4 Hz), 4.00 (m, 2 H), 3.75 (m, 2 H), 3.52 (t, 2 H, J=6.6 Hz), 2.00 (m, 2 H), 1.85 (m, 2 H); $^{13}$C NMR (CDCl$_3$) δ 141.0, 134.0, 128.5, 127.3, 109.7, 65.0, 45.1, 37.8, 27.0. Anal. Calcd for C$_{12}$H$_{14}$Cl$_2$O$_2$: C, 55.19; H, 5.40. Found: C, 55.28; H, 5.44.

[4]Li, et al., Huaxue Xuebao, 1990, 48, 913–919.

EXAMPLE 10

General Procedure for the Synthesis of ω-Haloalkylamines (II)

Mixtures of NHR$^1$R$^2$ (100 mmol), α-bromo-ω-chloroalkane (200 mmol), and K$_2$CO$_3$ (14 g, 100 mmol) in MeCN (200 mL) were refluxed overnight. The resulting mixtures were taken up in water and extracted with CH$_2$Cl$_2$. The organic extracts were then subjected to chromatography (SiO$_2$:CH$_2$Cl$_2$), and the isolated free bases were acidified with 1 N HCl/Et$_2$O. After solvent removal, the residues were dried overnight in a drying pistol to afford the alkylamino alkylating agents.

EXAMPLE 11

N-3-Chloropropyl-N-methylbenzenemethanamine Hydrochloride

Starting with N-methylbenzenemethanamine in the Example 10 procedure provides the product compound obtained as a white solid (30% yield): MS m/z 198.3 (MH$^+$); $^1$H NMR (DMSO-d$_6$) δ 11.10 (br s, 1 H), 7.61 (m, 2 H), 7.42 (m, 3 H), 4.29 (m, 2 H), 3.71 (t, 2 H, J=6.3 Hz), 3.15, 3.05 (m, 2 H), 2.61 (s, 3 H), 2.22 (m, 2 H); $^{13}$C NMR (DMSO-d$_6$) δ 131.6, 130.4, 129.8, 129.1, 58.6, 52.5, 42.8, 35.9, 26.7. Anal. Calcd for C$_{11}$H$_{16}$ClN. HCl: C, 56.42; H, 7.32; N, 5.98. Found: C, 56.49; H, 7.43; N, 5.88.

EXAMPLE 12

N-(3-Chloropropyl)-N-(phenylmethyl)benzenemethanamine Hydrochloride

This compound was isolated as a white solid (7% yield): MS m/z 274.2 (MH$^+$); $^1$H NMR (DMSO-d$_6$) δ 11.11 (br s,1 H), 7.62 (m, 4 H), 7.44 (m, 6 H), 4.31 (m, 4 H), 3.62 (t, 2 H, J=6.3 Hz), 3.00 (m, 2 H), 2.21 (m, 2 H), 2.21 (m, 2 H); $^{13}$C NMR (DMSO-d$_6$) δ 131.4, 129.8, 129.5, 128.8, 56.2, 48.9, 42.4, 25.9. Anal. Calcd for C$_{17}$H$_{20}$ClN. HCl. 0.5 H$_2$O: C, 63.95; H, 6.95; N, 4.39. Found: C, 63.92; H, 6.62; N, 4.15.

EXAMPLE 13

N-(2-Hydroxyethyl)-N-methylbenzenemethanamine[5]

A mixture of N-methylbenzenemethanamine (3.0 g, 25 mmol), 2-chloroethanol (3.0 mL, 45 mmol), KI (10 mg), and K$_2$CO$_3$ (4 g, 30 mmol) in MeCN (50 mL) was refluxed for 48 h. The reaction mixture was then taken up in water and extracted with CH$_2$Cl$_2$. The organic extract was dried (Na$_2$SO$_4$), and the solvent was removed in vacuo. The resulting alcohol was isolated by bulb-to-bulb distillation to afford a colorless oil (2.6 g, 63% yield): MS m/z 166.2 (MH$^+$); $^1$H NMR (CDCl$_3$) δ 7.33 (m, 5 H), 3.61 (t, 2 H, J=5.4 Hz), 2.86 (m, 1 H), 2.59 (t, 2 H, J=5.4 Hz), 2.22 (s, 3 H); $^{13}$C NMR (CDCl$_3$) 8138.8, 129.2, 128.5, 127.4, 62.5, 58.6, 58.5, 41.7. Anal. Calcd for C$_{10}$H$_{15}$NO. 0.1 H$_2$O: C, 71.91; H, 9.17; N, 8.39. Found: C, 71.57; H, 8.93; N, 8.15.

[5]Ofner, J. Chem. Soc., 1950, 2158, 2165.

Treatment with methanesulfonyl chloride and pyridine in CH$_2$Cl$_2$ provided the mesylate alkylating agent.

3. Diphenyl Ether Type Alkylating Agents (II)

EXAMPLE 14

General Procedure for the Synthesis of Diphenyl Ether Type Alkylating Agents (see Scheme 3)

To solutions of diphenyl ether (8.5 g, 50 mmol) in CCl$_4$ (150 mL) under N$_2$ was added AlCl$_3$ (7.3 g, 55 mmol), resulting in a cherry-red color. These reactions were cooled to 10° C., and solutions of either 2-chloroacetyl chloride (4.0 mL, 50 mmol) or 3-chloropropionyl chloride (4.8 mL, 50 mmol) in CCl$_4$ (50 mL) were added in a dropwise fashion over 30 min. The resulting mixtures were then gradually warmed to room temperature while stirring for 2 h, and then were quenched with ice. The aqueous extract was discarded, and the organic extract was rinsed with water and dried (Na$_2$SO$_4$), followed by solvent removal. The residues were subjected to chromatography (SiO$_2$:Hexanes/CH$_2$Cl$_2$) to afford the desired products.

EXAMPLE 15

2-Chloro-1-(4-phenoxyphenyl)ethanone[6]

This compound was isolated as a white solid (6.41 g, 52% yield): MS (DCl) m/z 247 (MH$^+$); $^1$H NMR (CDCl$_3$) δ 7.95 (d, 2 H, J=9.0 Hz), 7.42 (t, 2 H, J=7.5 Hz), 7.23 (t, 1 H, J=7.2 Hz), 7.10 (d, 2 H, J=7.8 Hz), 7.02 (d, 2 H, J=8.7 Hz), 4.67 (s, 2 H); $^{13}$C NMR (CDCl$_3$) δ 189.9, 163.0, 155.2, 131.2, 130.4, 128.8, 125.2, 120.6, 117.5, 46.0. Anal. Calcd for C$_{14}$H$_{11}$ClO$_2$: C, 68.16; H, 4.49. Found: C, 68.14; H, 4.59.

[6]See footnote (3).

EXAMPLE 16

3-Chloro-1-(4-phenoxyphenyl)propanone[7]

This compound was obtained as a white solid (4.06 g, 31% yield): MS (DCl) m/z 262 (MH$^+$); $^1$H NMR (CDCl$_3$) δ 7.94 (d, 2 H, J=8.7 Hz), 7.41 (t, 2 H, J=8.7 Hz), 7.22 (t, 1 H, J=8.7 Hz), 7.10 (d, 2 H, J=8.1 Hz), 7.03 (d, 2 H, J=9.0 Hz), 3.93 (t, 2 H, J=6.9 Hz), 3.43 (t, 2 H, J=6.6 Hz); $^{13}$C NMR (CDCl$_3$)δ 195.5, 162.6, 155.5, 131.2, 130.6, 130.3, 125.0, 120.5, 117.5, 41.2, 39.0. Anal. Calcd for C$_{15}$H$_{13}$ClO$_2$: C, 68.10; H, 5.03. Found: C, 68.77; H, 5.23.

[7]Allen, et al., Canad. J. Res., 1933, 8, 440–443.

II. Synthesis of Formula I Products

The following synthetic procedure describes the general method for reaction of compound III with compound II alkylating agents, as shown in Scheme 1 for preparation of Formula I product. Specific examples of use of this general method follow.

EXAMPLE 17

General Method—Alkylation Reactions

Mixtures of the appropriate alkyl iodide, bromide, chloride, or mesylate (II) (1.0 eq), K$_2$CO$_3$ (1.0 eq), and KI or NaI (0.1 eq added for alkyl chloride or mesylate) in MeCN were stirred with refluxing for 2–24 h. The reaction mixtures were either filtered directly onto silica gel cartridges for purification or extracted between CH$_2$Cl$_2$ and water, and the organic extract was subjected to flash chromatography, eluting the products with varying concentrations of MeOH: 30% aq NH$_3$ (9:1) in CH$_2$Cl$_2$. After solvent removal, most of the isolated products were taken up in MeOH and converted to the hydrochloride salts using 1 N HCl/Et$_2$O. This was generally followed by solvent removal, although in many cases the resulting salts readily crystallized from the methanolic solutions and were collected by filtration. The products thus obtained were further heated overnight in a drying pistol.

EXAMPLE 18

1'-[3-(4-Phenoxyphenyl)-3-oxopropyl]spiro [isoquinoline-1-(2H)-4'-piperidine-3-(4H)-one Hydrochloride Alkylation of III with 3-(4-phenoxyphenyl)-3-oxopropylchloride gave the compound as a white solid (79% yield): MS m/z 441.5 (MH$^+$); $^1$H NMR (DMSO-d$_6$) δ 11.30 (br s, 1 H), 8.33 (s, 1 H), 8.05 (d, 2 H, J=9.0 Hz), 7.47 (t, 2 H, J=8.1 Hz), 7.38 (t, 1 H, J=9.0 Hz), 7.25 (m, 4 H), 7.12 (m, 4 H), 3.71 (t, 2 H, J=7.2 Hz), 3.62 (s, 2 H), 3.48 (m, 6 H), 2.63 (m, 2 H), 1.97 (m, 2 H); $^{13}$C NMR (DMSO-d$_6$) δ 195.2, 169.7, 161.6, 154.9, 137.9, 132.1, 130.8, 130.7, 130.4, 128.1, 127.7, 127.0, 124.9, 123.4, 120.0, 117.3, 53.9, 50.9, 47.3, 36.0, 34.2, 32.7. Anal. Calcd for C$_{28}$H$_{28}$N$_2$O$_3$. 1.0 HCl. 0.5 H$_2$O: C, 69.20; H, 6.22; N, 5.76. Found: C, 69.17; H, 6.14; N, 5.71.

EXAMPLE 19

1'-[3-(4-Bromophenyl)-3-oxopropyl]spiro [isoquinoline-1-(2H)-4'-piperidine-3-(4H)-one]

This product of III and 3-chloro-4'-bromopropiophenone was isolated as a white solid (58% yield): MS m/z 428.4 (MH$^+$); $^1$H NMR (DMSO-d$_6$) δ 7.94 (d, 2 H, J=9.0 Hz), 7.86 (s, 1 H), 7.74 (d, 2 H, J=8.7 Hz), 7.40 (m, 1 H), 7.23 (m, 3 H), 3.55 (s, 2 H), 3.22 (t, 2 H, J=6.9 Hz), 2.76 (m, 4 H), 2.53 (m, 2 H), 1.99 (m, 2 H), 1.70 (m, 2 H); $^{13}$C NMR (DMSO-d$_6$) δ 198.7, 170.0, 140.5, 135.8, 132.5, 131.8, 130.0, 127.8, 127.2, 127.1, 126.7, 123.1, 55.2, 52.7, 48.0, 36.8, 36.1, 35.9. Anal. Calcd for C$_{22}$H$_{23}$BrN$_2$O$_2$. 0.25 H$_2$O: C, 61.19; H, 5.49; N, 6.49. Found: C, 61.21; H, 5.29; N, 6.29.

EXAMPLE 20

1'-[2-[(1,1'-Biphenyl)-4-yl]-2-oxoethyl]spiro [isoquinoline-1-(2H)-4'-piperidine-3-(4H)-one]

The reaction mixture from the alkylation of III with 2-bromo-4'-phenylacetophenone was diluted with water and then filtered. The solid thus collected was triturated in EtOAc and collected by filtration to afford a tan solid (56% yield): MS m/z 411.3 (MH$^+$); $^1$H NMR (DMSO-d$_6$) δ 8.11 (d, 2 H, J=8.4Hz), 7.84 (m, 3 H), 7.76 (d, 2 H, J=6.9 Hz), 7.52 (t, 2 H, J=6.9 Hz), 7.47 (m, 2 H), 7.26 (m, 3 H), 3.94 (br s, 2 H), 3.57 (s, 2 H), 2.82 (m, 2 H), 2.69 (m, 2 H), 2.08 (m, 2 H), 1.74 (m, 2 H); $^{13}$C NMR (DMSO-d$_6$) 6196.7, 170.1, 144.5, 140.5, 138.9, 134.7, 132.5, 129.1, 128.9, 128.4, 127.8, 127.0, 126.8, 126.7, 123.1, 63.9, 54.9, 48.3, 36.8, 35.9. Anal. Calcd for C$_{27}$H$_{26}$N$_2$O$_2$. 0.7 H$_2$O: C, 76.64; H, 6.53; N, 6.62. Found: C, 76.64; H, 6.40; N, 6.61.

EXAMPLE 21

1'-[2-(4-Bromophenyl)-2-oxoethyl]spiro [isoquinoline-1-(2H)-4'-piperidine-3-(4H)-one]

Following the alkylation of III with 2,4'-dibromoacetophenone, this compound was isolated by the method described above to afford a white solid (79% yield): MS m/z 413.3 (MH$^+$); $^1$H NMR (DMSO-d$_6$) δ 7.94 (d, 2 H, J=8.4 Hz), 7.80 (s, 1 H), 7.73 (d, 2 H, J=8.4 Hz), 7.41 (m, 1 H), 7.24 (m, 3 H), 3.86 (s, 2 H), 3.54 (s, 2 H), 2.76 (m, 2 H), 2.60 (m, 2 H), 2.02 (m, 2 H), 1.69 (m, 2 H); $^{13}$C NMR (DMSO-d$_6$) δ 196.9, 170.4, 140.8, 135.2, 132.9, 132.0, 130.6, 128.2, 127.6, 127.4, 127.1, 123.4, 64.3, 55.2, 48.6, 37.2, 36.3. Anal. Calcd for C$_{21}$H$_{21}$BrN$_2$O$_2$. 0.3 H$_2$O: C, 60.24; H, 5.20; N, 6.69. Found: C, 60.22; H, 5.23; N, 6.71.

EXAMPLE 22

1'-[2-(4-Phenoxyphenyl)-2-oxoethyl]spiro [isoquinoline-1-(2H-4'-piperidine-3-(4H)-one] Hydrochloride This compound, obtained from the reaction of III and 2-chloro-4'-phenoxyacetophenone, was isolated as a white solid (78% yield): MS m/z 427.4 (MH$^+$). Anal. Calcd for C$_{27}$H$_{26}$N$_2$O$_3$. HCl. 0.5 H$_2$O: C, 68.71; H, 5.98; N, 5.94. Found: C, 68.72; H, 5.98; N, 5.86.

EXAMPLE 23

1'-[2-[Bis(phenylmethyl)amino]ethyl]spiro [isoquinoline-1-(2H)-4'-piperidine-3-(4H)-one] Dihydrochloride This compound was obtained from the reaction of III and N,N-dibenzyl-2-chloroethylamine, and was isolated as a white solid (66% yield): MS m/z 440.4 (MH$^+$). Anal. Calcd for C$_{29}$H$_{33}$N$_3$O. 2.0 HCl. H$_2$O: C, 65.66; H, 7.03; N, 7.92. Found: C, 65.66; H, 7.02; N, 7.64.

The following synthetic procedure describes the general method for hydrolysis of the ketal precursors to afford Formula I compounds wherein R is

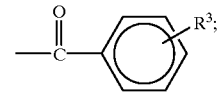

as shown in Scheme 2. Specific examples follow for illustration.

EXAMPLE 24

General Method—Hydrolysis of Ketal Products

The ketal products (XI) were taken up in a minimum of THF:1N HCl (2:1) and refluxed for 30 min. The reaction mixtures were then made basic (satd. Na$_2$CO$_3$) and extracted with CH$_2$Cl$_2$. The organic extracts were then dried (Na$_2$SO$_4$), and 1 eq of 1N HCl/Et$_2$O was added to each. The resulting hydrochloride salts of the Formula I products were crystallized from these solutions, collected by filtration, and dried overnight in a drying pistol.

Example 25

1'-(4-Phenyl-4-oxobutyl)spiro[isoquinoline-1-(2H)-4'-piperidine-3-(4H)-one] Hydrochloride This compound was obtained from the hydrolysis of ketal products (XI) to afford a white solid (45% yield): MS m/z 363.2 (MH$^+$); HPLC purity 95.9%.

EXAMPLE 26

1'-[4-(4-Methoxyphenyl)-4-oxobutyl]spiro[isoquinoline-1-(2H)-4'-piperidine-3-(4H)-one] Hydrochloride This compound was derived from the corresponding dioxolane to furnish a white solid (98% yield): MS m/z 393.2 (MH$^+$); HPLC purity 91.3%.

EXAMPLE 27

1'-[4-(4-Phenoxyphenyl)-4-oxobutyl]spiro[isoquinoline-1-(2H)-4'-piperidine-3-(4H)-one] Hydrochloride The deprotection of the corresponding dioxolane gave this compound as a white solid (quant.): MS m/z 455.2 (MH$^+$); HPLC purity 95.3%.

EXAMPLE 28

1'-[4-(4-Bromophenyl)-4-oxobutyl]spiro[isoquinoline-1-(2H)-4'-piperidine-3-(4H)-one]

This compound was synthesized by the alkylation with the dioxolone of Example 8 to afford the ketal precursor, which was subsequently hydrolyzed to the desired ketone product by the method described above to afford the free base as a white solid (48% yield, 2 steps): MS m/z 441.2, 443.3 (MH$^+$); $^1$H NMR (DMSO-d$_6$) δ 7.93 (d, 2 H, J=8.7Hz), 7.74 (m, 3 H), 7.27 (m, 2 H), 7.20 (m, 1 H), 7.10 (m, 1 H), 3.51 (s, 2 H), 3.17 (t, 2 H, J=7.5 Hz), 2.61 (m, 2 H), 2.39 (m, 4 H), 1.85 (m, 2 H), 1.68 (m, 2 H); $^{13}$C NMR (DMSO-d$_6$) δ 198.8, 169.9, 140.5, 136.3, 132.5, 131.7, 130.1, 127.8, 127.0, 126.8, 126.6, 122.9, 57.0, 55.2, 47.9, 36.8, 35.9, 35.6, 22.2. Anal. Calcd for C$_{23}$H$_{25}$BrN$_2$O$_2$: C, 62.59; H, 5.71; N, 6.35. Found: C, 62.42; H, 5.85; N, 6.27.

EXAMPLE 29

1'-[4-(4-Chlorophenyl)-4-oxobutyl]spiro[isoquinoline-1-(2H)-4'-piperidine-3-(4H)-one] Hydrochloride The deprotection of the corresponding dioxolane furnished this compound as a white solid (86% yield): MS m/z 397.2, 399.3 (MH$^+$); HPLC purity 90.2%.

The following synthetic procedure describes further structural elaboration of Formula I products containing an aryl halide moiety as part of R. The procedure is shown in Scheme 4. Several specific examples of the procedure are given following the general method.

EXAMPLE 30

General Method—Further Elaboration of Formula I Products

Solutions of Formula I compounds containing arylbromide moieties (1.0 eq), phenylboronic acid (1.1 eq), and Pd(PPh$_3$)$_4$ (0.05 eq) in EtOH: 2M Na$_2$CO$_3$ (1:1, 50 ml/eq) were refluxed for 1–18 h. The reaction mixtures were cooled, and 30% aq H$_2$O$_2$ (5 ml/eq)was added, followed by stirring for 1 h (No H$_2$O$_2$ was added to the reaction mixture, producing the 4-phenyl-phenyl product.) The reaction mixtures were then extracted with CH2Cl$_2$, and the organic extracts were dried (Na$_2$SO$_4$), followed by solvent removal. The residues were then subjected to flash chromatography (SiO$_2$:CH$_2$Cl$_2$/MeOH/30% aq NH$_3$). After solvent removal, the residues were taken up in CH$_2$Cl$_2$, to which was added 1N HCl/Et$_2$O (1 eq). The biphenyl products were crystallized from these solutions, collected by filtration, and dried overnight in a drying pistol.

EXAMPLE 31

1'-[2-[(1,1'-Biphenyl)-3-yl]-2-oxoethyl]spiro[isoquinoline-1-(2H)-4'-piperidine-3-(4H)-one] Hydrochloride This compound was synthesized from the compound wherein R is a 3-bromophenacyl moiety to afford a tan solid (22% yield): MS m/z 411.4 (MH$^+$); $^1$H NMR (DMSO-d$_6$) δ 10.32 (br s, 1 H), 8.34 (s, 1 H), 8.25 (s, 1 H), 8.08 (d, 1 H, J=7.8 Hz), 8.02 (d, 1 H, J=7.8 Hz), 7.77 (t, 2 H, J=7.2 Hz), 7.55 (m, 2 H), 7.48 (m, 2 H), 7.37 (m, 2 H), 7.30 (m, 2 H), 5.16 (br s, 2 H), 3.63 (s, 2 H), 3.59 (m, 2 H), 3.50 (m, 2 H), 2.63 (m, 2 H), 2.03 (m, 2 H); $^{13}$C NMR (DMSO-d$_6$) δ 191.5, 170.0, 141.0, 138.9, 138.2, 134.5, 132.9, 132.3, 129.8, 129.2, 128.8, 128.2, 127.7, 127.0, 126.9, 126.5, 123.2, 53.6, 48.9, 48.6, 36.2, 33.7. Anal. Calcd for C$_{27}$H$_{26}$N$_2$O$_2$. HCl. 1.2 H$_2$O: C, 69.21; H, 6.32; N, 5.98. Found: C, 69.19; H, 6.10; N, 6.05.

EXAMPLE 32

1'-[3-[(1,1'-Biphenyl)-4-yl]-3-oxopropyl]spiro[isoquinoline-1-(2H)-4'-piperidine-3-(4H)-one] Hydrochloride This compound was prepared from the Formula I compound where Z is 4-bromophenacylpropyl to afford a white solid (15% yield): MS m/z 425.3 (MH$^+$); 85.7% HPLC purity.

EXAMPLE 33

1'-[4-[(1,1'-Biphenyl)-4-yl]-4-oxobutyl]spiro[isoquinoline-1-(2H)4'-piperidine-3-(4H)-one] Hydrochloride This compound was synthesized from the Formula I compound where Z is 4-bromophenocylbutyl to furnish a white solid (53% yield): MS m/z 439.3 (MH$^+$); 98.6% HPLC purity.

EXAMPLE 34

1'-[2-[(1,1'-Biphenyl)-4-yl]-2-hydroxyethyl]spiro[isoquinoline-1-(2H)-4'-piperidine-3-(4H-one] Hydrochloride A suspension of Formula I compound where Z is 4-bromophenacylethyl (205 mg, 0.50 mmol) and MeOH-rinsed Raney Nickel in MeOH (30 mL) was hydrogenated in a Parr apparatus at 50 psi for 2 h, and the catalyst was removed by filtration over Celite. The filtrate was then passed through a SCX cation-exchange cartridge to remove any neutral impurities, and then the desired product was eluted with CH$_2$Cl$_2$:MeOH:30% aq NH$_3$ (97.5:2.3:0.2).

After solvent removal, the residue was taken up in MeOH and combined with 1N HCl/Et$_2$O (0.5 mL). The solvent was removed in vacuo to afford the racemic alcohol product as a white solid (42 mg, 19% yield): MS m/z413.3 (MH$^+$); $^1$H NMR (DMSO-d$_6$) δ 10.34 (br s,1 H), 8.26 (s, 1 H), 7.70 (m, 4 H), 7.53 (m, 2 H), 7.43 (m, 2 H), 7.33 (m, 4 H), 7.24 (m, 1 H), 6.35 (d, 1 H, J=3.9 Hz), 5.3 (m,1 H), 3.67 (m, 2 H), 3.61 (s, 2 H), 3.56 (m, 2 H), 3.29 (m, 2 H), 2.65 (m, 2 H), 1.99 (m, 2 H); $^{13}$C NMR (DMSO-d$_6$) 6169.8, 140.8, 139.8, 138.1, 132.1, 129.0, 128.1, 127.7, 126.7, 126.6, 123.3, 53.8, 48.8, 48.6, 46.9, 36.0, 34.0. Anal. Calcd for C$_{27}$H$_{28}$N$_2$H$_2$·HCl. 0.75 H$_{2O}$: C, 70.12; H, 6.65; N, 6.06. Found: C, 70.26; H, 6.66; N, 5.82.

EXAMPLE 35

Receptor Binding Assay

Human cDNA of the NPY Y$_5$ receptor was PR-corrected in Baculovirus which was then used to infect "Hi5" (BTI-TN-5BI-4) insect cells during 48 hr incubation. The cells were harvested and used for the binding assay using iodine-125-labeled-PYY ([$^{125}$I]PYY) as a radioligand. Saturation binding used 0.05–100 nM [$^{125}$I]PYY. Nonspecific binding was determined in the presence of 1000 nM unlabeled PYY and was less than 20% of total binding.

Using the above-described methods, a number of additional Formula I products were synthesized and are listed in Table 1.

TABLE 1

Additional Formula I Compounds

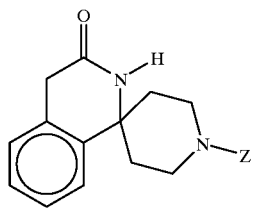

I

| Example No. | Z | % Yield |
|---|---|---|
| 36 | n-nonyl | 58 |
| 37 | n-decyl | 50 |
| 38 | allyl | 39 |
| 39 | 3-phenyl-2-propenyl | 51 |
| 40 | 6-phenylhexyl | 11 |
| 41 | —CH$_2$CH(OMe)$_2$ | 18 |
| 42 | —CH$_2$CH$_2$OH | 18 |
| 43 | 1-adamantanacetyl | 59 |
| 44 | PhCO$_2$—⬡—CO—CH$_2$CH$_2$ | 64 |
| 45 | Et$_2$N—⬡—COCH$_2$CH$_2$ | 79 |
| 46 | (PhCH$_2$)$_2$—N—(CH$^2$)$_4$— | 28 |

What is claimed is:

1. A compound of Formula I and its pharmaceutically

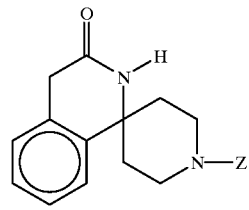

I acceptable acid addition salts and/or hydrates thereof, wherein

Z is selected from C$_{9-10}$alkyl, C$_{2-6}$alkenyl, and —AR; in which A is C$_{1-6}$ alkanediyl and C$_{2-6}$alkenediyl; and R is —OH, —CH(OMe)$_2$, —NR$^1$R$^2$, 1-adamantyl,

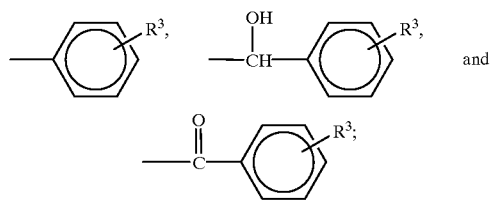

with R$^1$ and R$^2$ are independently chosen from H, benzyl and C$_{1-4}$alkyl; and R$^3$ is selected from hydrogen, C$_{1-4}$alkyl, C$_{1-4}$alkoxy, —NR$^1$R$^2$, halogen, phenyl, phenoxy, and —O$_2$C-phenyl;
with the proviso that then R is

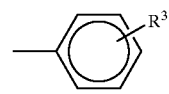

R$^3$ cannot be H and when R is

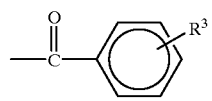

R$^3$ cannot be H, halogen or alkoxy.

2. The compound of claim 1 wherein A is a methyl or ethyl group.

3. The compound of Formula I wherein R is

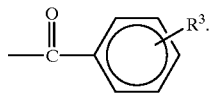

4. The compound of claim 3 wherein R$^3$ is attached at the p-position of the phenyl ring.

5. The compound of claim 4 wherein R$^3$ is phenyl or phenoxy.

6. A method of promoting weight loss and treating eating disorders in a mammal comprising administration to a mammalian host of an effective anorexiant dose of a compound of Formula I and its pharmaceutically

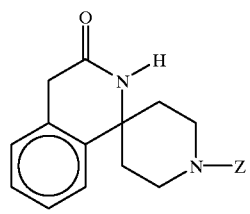

acceptable acid addition salts and/or hydrates thereof, wherein

Z is selected from $C_{9\text{-}10}$alkyl, $C_{2\text{-}6}$alkenyl, and —AR; in which A is $C_{1\text{-}6}$ alkanediyl and $C_{2\text{-}6}$alkenediyl; and R is —OH, —CH(OMe)$_2$, —NR$^1$R$^2$, 1-adamantyl,

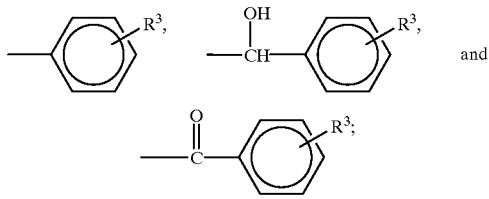

and with R$^1$ and R$^2$ are independently chosen from H, benzyl and $C_{1\text{-}4}$alkyl; and R$^3$ is selected from hydrogen, $C_{1\text{-}4}$alkyl, $C_{1\text{-}4}$alkoxy, —NR$^1$R$^2$, halogen, phenyl, phenoxy, and —O$_2$C-phenyl.

7. A method of promoting weight loss and treating eating disorders in a mammal comprising administration to a mammalian host of an effective anorexiant dose of a compound claimed in claim 1.

8. A method of promoting weight loss and treating eating disorders in a mammal comprising administration to a mammalian host of an effective anorexiant dose of a compound claimed in claim 5.

9. A pharmaceutical composition for use in promoting weight loss and treating eating disorders, the composition comprising an effective anorexiant amount of a Formula I compound claimed in claim 1 in combination with a pharmaceutically acceptable carrier.

10. A pharmaceutical composition for use in promoting weight loss and treating eating disorders, the composition comprising an effective anorexiant amount of a compound claimed in claim 5 in combination with a pharmaceutically acceptable carrier.

* * * * *